United States Patent
Niskanen et al.

(10) Patent No.: US 11,103,162 B2
(45) Date of Patent: Aug. 31, 2021

(54) METHOD, APPARATUS AND COMPUTER PROGRAM PRODUCT FOR ACTIVITY RECOGNITION

(71) Applicant: Nokia Technologies Oy, Espoo (FI)

(72) Inventors: Antti Niskanen, Cambridge (GB); Joachim Wabnig, Upper Cambourne (GB)

(73) Assignee: NOKIA TECHNOLOGIES OY, Espoo (FI)

( * ) Notice: Subject to any disclaimer, the term of this patent is extended or adjusted under 35 U.S.C. 154(b) by 746 days.

(21) Appl. No.: 14/333,471

(22) Filed: Jul. 16, 2014

(65) Prior Publication Data
US 2015/0039260 A1    Feb. 5, 2015

(30) Foreign Application Priority Data
Aug. 2, 2013   (GB) .................................... 1313827

(51) Int. Cl.
*A61B 5/11*        (2006.01)
*G06K 9/00*        (2006.01)
(Continued)

(52) U.S. Cl.
CPC ........ *A61B 5/1123* (2013.01); *G06K 9/00523* (2013.01); *G06K 9/00536* (2013.01); *G06K 9/6244* (2013.01); *H03M 7/3062* (2013.01)

(58) Field of Classification Search
CPC ............ H03M 7/3062; G06K 9/00536; G06K 9/00523; G06K 9/6244; G06K 9/00973; G06K 15/1219
See application file for complete search history.

(56) References Cited

U.S. PATENT DOCUMENTS

| 7,477,999 B2 * | 1/2009 | Wegener ............. G01R 13/029 702/66 |
| 8,610,074 B2 * | 12/2013 | Nogueira-Nine .... G01K 11/006 250/358.1 |

(Continued)

FOREIGN PATENT DOCUMENTS

| CN | 1877340 | 12/2006 |
| CN | 101252430 A | 8/2008 |

(Continued)

OTHER PUBLICATIONS

Xu et al., "Co-Recognition of Human Activity and Sensor Location via Compressed Sensing in Wearable Body Sensor Networks," IEEE (2012).*

(Continued)

*Primary Examiner* — Brent A. Fairbanks
(74) *Attorney, Agent, or Firm* — Alston & Bird LLP

(57) ABSTRACT

In accordance with an example embodiment a method, apparatus and computer program product are provided. The method comprises receiving, at an apparatus, a sampled data associated with an activity from one or more sensors wirelessly coupled to the apparatus. The sampled data is generated at the one or more sensors based on a compressive sampling of an activity data associated with the activity. The compressive sampling is performed based on a sampling information. The activity is classified based at least on the sampled data. An error associated with the classification of the activity is determined. The sampling information is updated or retained based on a comparison of the error with a threshold error. The updated sampling information is utilized for generating an updated sampled data. The updated sampled data facilitates in reclassification of the activity.

22 Claims, 8 Drawing Sheets

(51) Int. Cl.
  *G06K 9/62* (2006.01)
  *H03M 7/30* (2006.01)

(56) References Cited

U.S. PATENT DOCUMENTS

| | | | |
|---|---|---|---|
| 2006/0284979 A1 | 12/2006 | Clarkson | |
| 2008/0228446 A1* | 9/2008 | Baraniuk | G06K 9/00523 702/189 |
| 2008/0288493 A1* | 11/2008 | Yang | G06K 9/00335 |
| 2010/0082302 A1 | 4/2010 | Garudadri et al. | |
| 2010/0176952 A1* | 7/2010 | Bajcsy | A61B 5/6887 340/573.1 |
| 2010/0184563 A1* | 7/2010 | Molyneux | A43B 5/02 482/1 |
| 2010/0246920 A1* | 9/2010 | Vaswani | H03M 7/30 382/131 |
| 2011/0066381 A1* | 3/2011 | Garudadri | A61B 5/0002 702/19 |
| 2012/0005248 A1* | 1/2012 | Garudadri | H03M 7/30 708/207 |
| 2012/0183032 A1* | 7/2012 | Yedlapalli | G06F 17/141 375/224 |
| 2012/0254100 A1* | 10/2012 | Grokop | A61B 5/1123 706/52 |
| 2013/0066815 A1* | 3/2013 | Oka | H04M 1/72569 706/12 |
| 2013/0163645 A1* | 6/2013 | Kuo | H04L 25/03949 375/219 |
| 2013/0184558 A1* | 7/2013 | Gallant | A61B 5/0042 600/409 |
| 2014/0081592 A1* | 3/2014 | Bellusci | G01R 33/0064 702/141 |
| 2014/0358473 A1* | 12/2014 | Goel | G06F 3/05 702/141 |
| 2014/0361905 A1* | 12/2014 | Sadasivam | G08C 17/02 340/870.01 |
| 2015/0057967 A1* | 2/2015 | Albinali | A61B 5/1118 702/150 |
| 2015/0078489 A1* | 3/2015 | Zhu | H03M 7/3062 375/340 |
| 2015/0334580 A1 | 11/2015 | Niskanen et al. | |

FOREIGN PATENT DOCUMENTS

| | | |
|---|---|---|
| CN | 102625667 A | 8/2012 |
| CN | 102713914 A | 10/2012 |
| EP | 2265173 A1 | 12/2010 |
| JP | 2009-039466 A | 2/2009 |
| JP | 2009-230169 A | 10/2009 |
| JP | 2011-034402 A | 2/2011 |
| JP | 2012-118838 A | 6/2012 |
| KR | 2012-0065399 A | 6/2012 |
| KR | 10-1181301 B1 | 9/2012 |
| WO | 2009/128000 A1 | 10/2009 |
| WO | 2011/085368 A1 | 7/2011 |
| WO | 2011/116018 A1 | 9/2011 |

OTHER PUBLICATIONS

Akimura et al., "Compressed Sensing Method for Human Activity Sensing using Mobile Phone Accelerometers," IEEE (2010).*
Eldar et al., "Compressed Sensing: Theory and Applications", 1 Edition, Cambridge University Press, Jun. 29, 2012, 555 pages.
Donoho, "Compressed Sensing", IEEE Transactions on Information Theory, vol. 52, No. 4, Apr. 2006, pp. 1289-1306.
Search Report received for corresponding European Patent Application No. 14177747.4, dated Jan. 21, 2015, 7 pages.
Office action received for corresponding Korean Patent Application No. 2014-0099122, dated Apr. 27, 2015, 5 pages of office action and no pages of office action translation available.
Allowance received for corresponding Korean Patent Application No. 2014-0099122, dated Nov. 5, 2015, 2 pages of office action and 1 pages of office action translation available.
Office action received for corresponding Japanese Patent Application No. 2014-148528, dated Dec. 17, 2015, 2 pages of office action and no pages of office action translation available.
Allowance received for corresponding Japanese Patent Application No. 2014-148528, dated Jun. 2, 2016, 2 pages of office action and no page of office action translation available.
Office action received for corresponding Chinese Patent Application No. 201410379675.1, dated Nov. 28, 2016, 10 pages of office action and no pages of office action translation available.
PCT Application No. PCT/FI2012/051252, "Methods, Apparatus and Computer Programs for Obtaining Data", filed on Dec. 17, 2012, 35 pages.
Akimura et al., "Compressed Sensing Method for Human Activity Sensing Using Mobile Phone Accelerometers", Ninth International Conference on Networked Sensing Systems, Jun. 11-14, 2012, 4 pages.
Search Report received for corresponding United Kingdom Patent Application No. 1313827.6, dated Feb. 12, 2014, 4 pages.
Bingham et al., "Random Projection in Dimensionality Reduction: Applications to Image and Text Data", Proceedings of the seventh ACM SIGKDD International Conference on Knowledge Discovery and Data Mining, 2001, 6 pages.
Fradkin et al., "Experiments with Random Projections for Machine Learning", Proceedings of the ninth ACM SIGKDD International Conference on Knowledge Discovery and Data Mining, 2003, 8 pages.
Goel et al., "Face Recognition Experiments with Random Projection", Proceedings of the SPIE, vol. 5779, Mar. 2005, 12 pages.
Schclar et al., "Random Projection Ensemble Classifiers", Enterprise Information Systems, Lecture Notes in Business Information Processing, vol. 24, 2009, pp. 1-8.
Calderbank et al., "Compressed Learning: Universal Sparse Dimensionality Reduction and Learning in the Measurement Domain", Technical Report, Rice University, 2009, 10 pages.
Rahimi et al., "Random Features for Large-Scale Kernel Machines", In Neural Information Processing Systems, 2007, pp. 1-8.
Durrant et al., "Random Projections as Regularizers: Learning a Linear Discriminant Ensemble from Fewer Observations than Dimensions", Journal of Machine Learning Research, Draft, 2012, pp. 1-29.
Thanou et al., "Compressed Classification of Observation Sets With Linear Subspace Embeddings", IEEE International Conference on Acoustics, Speech and Signal Processing, May 22-27, 2011, 4 pages.
Xu et al., "Co-Recognition of Human Activity and Sensor Location via Compressed Sensing in Wearable Body Sensor Networks", Ninth International Conference on Wearable and Implantable Body Sensor Networks, May 9-12, 2012, pp. 124-129.
Concha et al., "Compressive Sensing of Time Series for Human Action Recognition", International Conference on Digital Image Computing: Techniques and Applications, Dec. 1-3, 2010, pp. 1-11.
Candes et al.. "An Introduction to Compressive Sampling", IEEE Signal Processing Magazine, Mar. 21, 2008, pp. 21-30.
Calderbank et al. "Finding Needles in Compressed Haystacks" Compressed Sensing: Theory and Applications, Chapter 10. (A shortened version of this article is provided herewith from IEEE 2012, pp. 3441-3444 and original chapter of the book is not provided herewith).
Office Action received for corresponding Chinese Patent Application No. 201410379675.1, dated Jun. 19, 2017, with English translation, 17 pages.
Theodoridis, S. et al. *Pattern Recognition*, Feature Selection (Chapter 5) and Feature Generation II (Chapter 7), Elsevier-Acad. Press, Amsterdam [U.A] (2009) pp. 275-288; 423-442.
Office Action for European Application No. 14177747.4 dated May 20, 2019, 9 pages.
Communication Pursuant to Article 94(3) EPC for European Patent Application No. 14177747.4 dated Apr. 21, 2021, 6 pages.

* cited by examiner

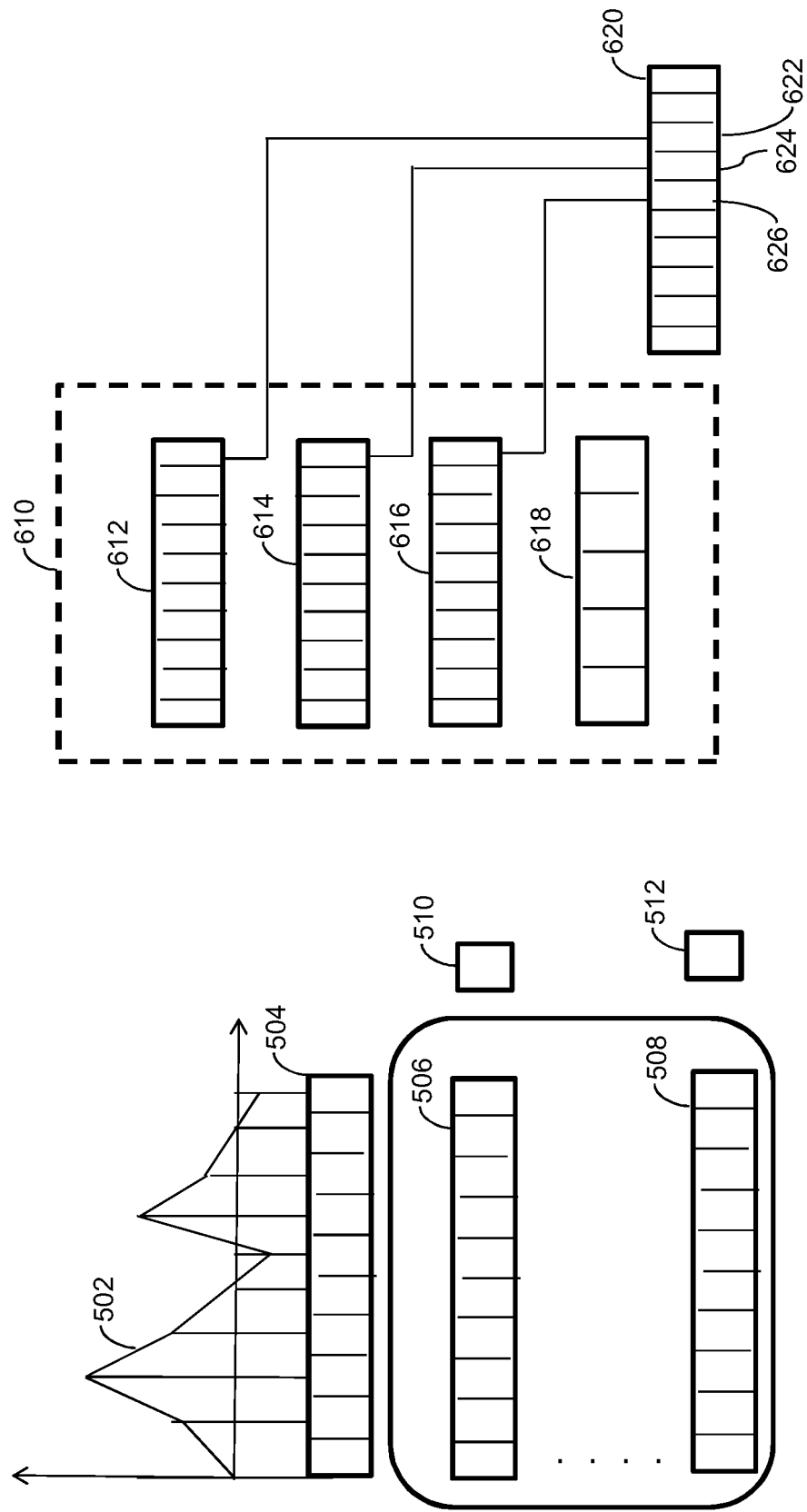

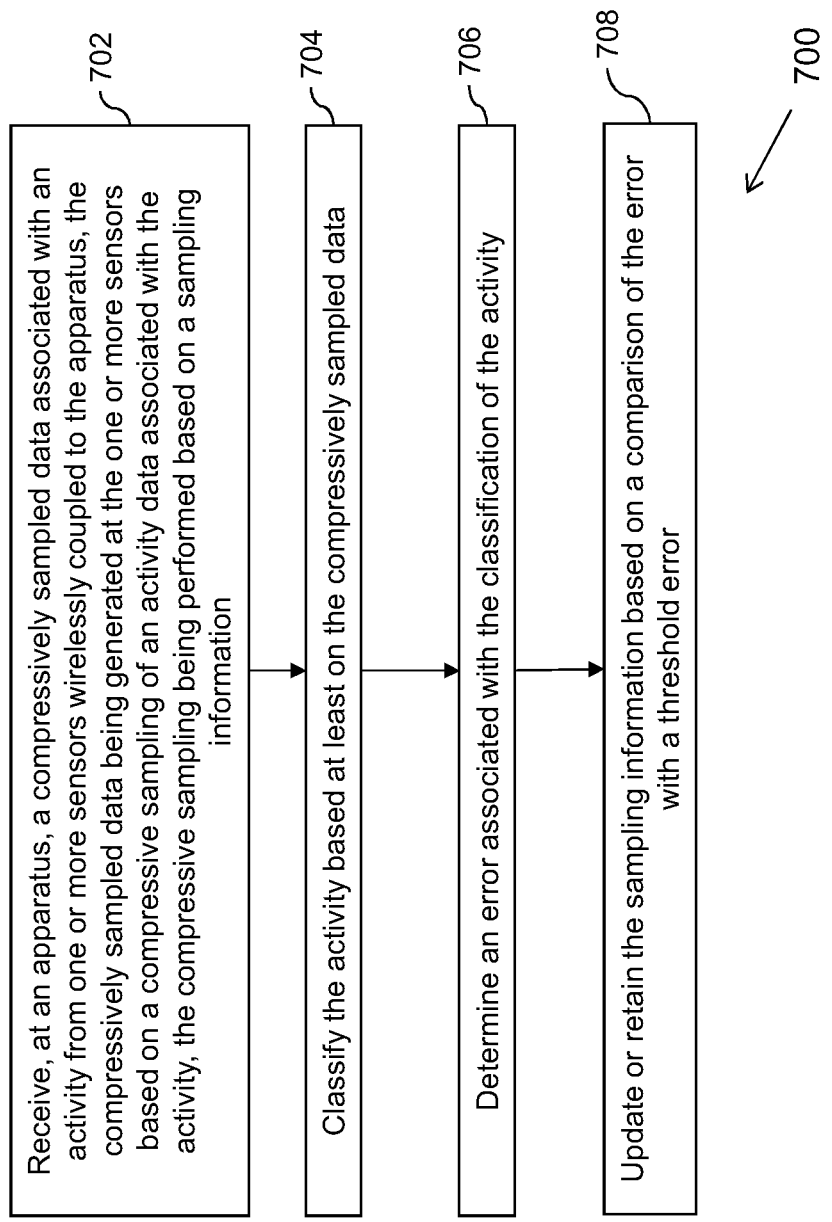

METHOD, APPARATUS AND COMPUTER PROGRAM PRODUCT FOR ACTIVITY RECOGNITION

TECHNICAL FIELD

Various implementations relate generally to method, apparatus, and computer program product for activity recognition.

BACKGROUND

In recent years, there has been a tremendous growth in the technology related to context-awareness based applications such as activity recognition. Activity recognition helps in identifying user needs based on sensing of human activities. Applications of activity recognition may include various real-life human centric problems/situations such as healthcare, elder-care, household activities, and the like. It may be desirable to provide reliable, cost-effective and energy efficient solutions for such human centric problems through activity recognition.

SUMMARY OF SOME EMBODIMENTS

Various aspects of example embodiments are set out in the claims.

In a first aspect, there is provided a method comprising: receiving, at an apparatus, a sampled data associated with an activity from one or more sensors wirelessly coupled to the apparatus, the sampled data being generated at the one or more sensors based on a compressive sampling of an activity data associated with the activity, the compressive sampling being performed based on a sampling information; classifying the activity based at least on the sampled data; determining an error associated with the classification of the activity; and updating or retaining the sampling information based on a comparison of the error with a threshold error.

In a second aspect, there is provided a method comprising: receiving, at a sensor, a sampling information from an apparatus wirelessly coupled to the sensor; performing compressive sampling of an activity data associated with an activity based at least on the sampling information and a sampling criteria for generating a sampled data associated with the activity; and sending the sampled data to the apparatus for facilitating classification of the activity.

In a third aspect, there is provided an apparatus comprising at least one processor; and at least one memory comprising computer program code, the at least one memory and the computer program code configured to, with the at least one processor, cause the apparatus to at least perform: receive, at an apparatus, a sampled data associated with an activity from one or more sensors wirelessly coupled to the apparatus, the sampled data being generated at the one or more sensors based on a compressive sampling of an activity data associated with the activity, the compressive sampling being performed based on a sampling information; classify the activity based at least on the sampled data; determine an error associated with the classification of the activity; and update or retain the sampling information based on a comparison of the error with a threshold error.

In a fourth aspect, there is provided an apparatus comprising at least one processor; and at least one memory comprising computer program code, the at least one memory and the computer program code configured to, with the at least one processor, cause the apparatus to at least perform: receive, at the apparatus, a sampling information from another apparatus wirelessly coupled to the apparatus; perform compressive sampling of an activity data associated with an activity based at least on the sampling information and a sampling criteria for generating a sampled data associated with the activity; and send the sampled data to the another apparatus for facilitating classification of the activity.

In a fifth aspect, there is provided a computer program product comprising at least one computer-readable storage medium, the computer-readable storage medium comprising a set of instructions, which, when executed by one or more processors, cause an apparatus to at least perform: receive, at an apparatus, a sampled data associated with an activity from one or more sensors wirelessly coupled to the apparatus, the sampled data being generated at the one or more sensors based on a compressive sampling of an activity data associated with the activity, the compressive sampling being performed based on a sampling information; classify the activity based at least on the sampled data; determine an error associated with the classification of the activity; and update or retain the sampling information based on a comparison of the error with a threshold error.

In a sixth aspect, there is provided a computer program product comprising at least one computer-readable storage medium, the computer-readable storage medium comprising a set of instructions, which, when executed by one or more processors, cause an apparatus to at least perform: receive, at the apparatus, a sampling information from another apparatus wirelessly coupled to the apparatus; perform compressive sampling of an activity data associated with an activity based at least on the sampling information and a sampling criteria for generating a sampled data associated with the activity; and send the sampled data to the another apparatus for facilitating classification of the activity.

In a seventh aspect, there is provided an apparatus comprising: means for receiving, at an apparatus, a sampled data associated with an activity from one or more sensors wirelessly coupled to the apparatus, the sampled data being generated at the one or more sensors based on a compressive sampling of an activity data associated with the activity, the compressive sampling being performed based on a sampling information; means for classifying the activity based at least on the sampled data; means for determining an error associated with the classification of the activity; and means for updating or retaining the sampling information based on a comparison of the error with a threshold error.

In an eighth aspect, there is provided an apparatus comprising: means for receiving, at the apparatus, a sampling information from another apparatus wirelessly coupled to the apparatus; means for performing compressive sampling of an activity data associated with an activity based at least on the sampling information and a sampling criteria for generating a sampled data associated with the activity; and means for sending the sampled data to the another apparatus for facilitating classification of the activity.

BRIEF DESCRIPTION OF THE FIGURES

Various embodiments are illustrated by way of example, and not by way of limitation, in the figures of the accompanying drawings in which:

FIG. 5 illustrates an example of compressive sampling of an activity data associated with activity recognition, in accordance with an example embodiment;

FIG. 6 illustrates a sequence of transmission of sampled data in accordance with an embodiment;

FIG. 7 is a flowchart depicting an example method for activity recognition, in accordance with an example embodiment;

DETAILED DESCRIPTION

Example embodiments and their potential effects are understood by referring to FIGS. 1 through 9 of the drawings.

Figure 1:
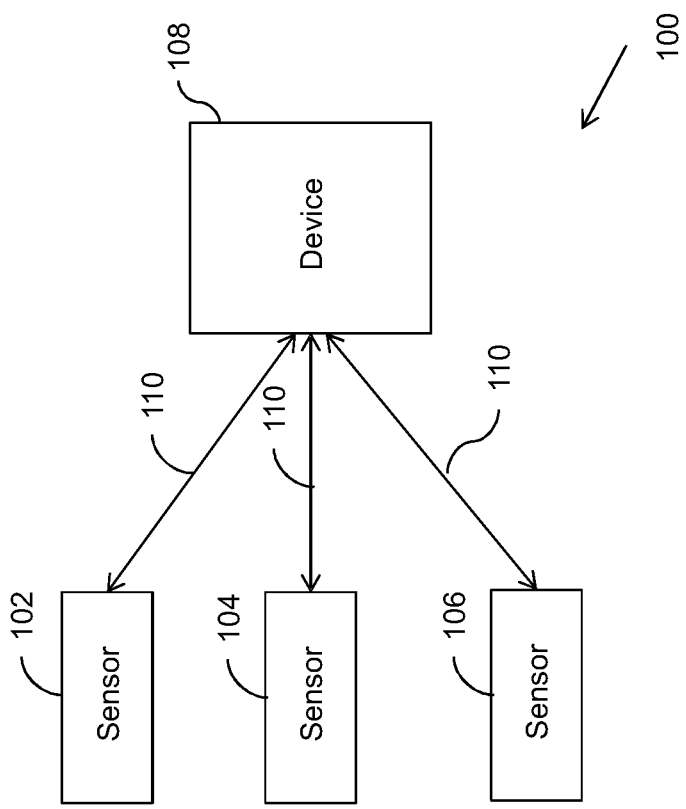
FIG. 1 illustrates an exemplary system for activity recognition in accordance with an example embodiment.

FIG. 1 illustrates an exemplary system 100 for performing activity recognition in accordance with an example embodiment. In an example embodiment, the system 100 may be configured to facilitate activity recognition based on sensing of an activity data associated with an activity, for example, a human activity. In particular, the purpose of activity recognition is to infer human behaviors from the activity data that may be acquired through one or more sensors in a given setting, based on which various decisions may be made. In an example embodiment, the information about the user's activities may be utilized to provide activity-dependent user experiences. For instance, based on activity recognition, if the user is determined to be running, then a user interface (UI) of a device coupled with the activity recognition sensors may adjust to a more accessible format.

As illustrated in FIG. 1, the system 100 includes one or more sensors, for example, sensors 102, 104, 106, communicably coupled with a device for example, a device 108. In an embodiment, the device 108 may be any kind of equipment that is able to communicate with the one or more sensors. In an embodiment, the device may be a smartphone, a laptop, a mobile phone a personal digital assistant (PDA), and the like. In an embodiment the one or more sensors may be coupled with the device through a communication path. In an embodiment, the communication path may be a wireless link, for example, a wireless link 110. In an embodiment, the wireless link 110 may include a radio link access network of a wireless communication network. Examples of wireless communication network may include, but are not limited to a cellular communication network. The communication path may additionally include other elements of a wireless communication network and even elements of a wire-line communication network to which the wireless communication network is coupled.

The one or more sensors may be configured to acquire activity data associated with a human activity. In an example embodiment, the activity data may include measurement data associated with an activity, for example, motion, temperature, location, and the like. In an embodiment, the one or more sensors may be configured to sample the activity data and in response generate a sampled data. In an embodiment, the sampled data may be generated by performing compressive sampling on the activity data using random basis vectors.

As used herein, compressive sampling/sensing facilitates in data compression and reconstruction. According to compressive sensing theorem, when an original signal can be expressed as a large number of zero or nearly zero values and a small number of non-zero values, the signals is said to be "sparse". Compressive sensing exploits the fact that many natural signals are sparse or compressible and as such these signals have concise representations when expressed in the appropriate basis. Sampling at a rate below the Nyquist frequency in a basis that is "incoherent" to the "sparse" basis facilitates in collecting all the relevant data and allows reconstruction of the original signal. As such, compressing sensing facilitates in reducing an amount of activity data being sampled by the one or more sensors, thereby reducing computational requirement at the one or more sensors. The sampled data that is being generated by the one or more sensors may hereinafter be referred to sampled data. As such, the terms 'sampled data' and 'compressively sampled data' may be used interchangeably throughout the description.

In an embodiment, the sampled data generated by the one or more sensors may be sent to the device 108. In an embodiment, the sampled data may be sent to the device 108 via a wireless link, such as the link 110. Based on the sampled data received from one or more sensors, the device 108 classifies an "activity" of the user, and assigns a label to the activity. In an embodiment, the term activity may include various examples such as running, walking, climbing up or down the stairs, jogging, cooking, opening a refrigerator, and the like. In general, any condition depicting an action and/or a movement by the user may be referred to as an activity, and accordingly the cited examples should not be construed as limiting to the present disclosure.

In an embodiment, the sampled data may be directly utilized for performing classification, without performing decompression of the sampled data. The preclusion of a need to decompress the sampled data prior to classification is advantageous in lowering the computational processing and power requirement of the device 108. Additionally, since the data is compressively sampled at the one or more sensors, it can be economically transmitted and stored on the device.

In an embodiment, the information associated with the activity may be used to provide activity-dependent user experiences. For instance, if the user is considered to be running, a user interface of the device 108 may adjust to a format that may be easily accessed by the user. In an example embodiment, only a selected one or more sensors may sample respective activity data associated with the activity of the user, and send the respective sampled data to the device 108. In an alternate example embodiment, multiple sensors coupled with the device 108 may sample the respective activity data and send the respective sampled data to the device 108. It will be understood that herein the one or more sensors (or multiple sensors) refers to various distinct sensors that are configured to sense different physical quantities. In an embodiment, the one or more sensors that are configured to send the corresponding sampled data to the device 108 may operate in synchronization. For example, when multiple sensors are operating for sensing and collecting the data, the timing of the multiple sensors may be synchronized.

Figure 2:
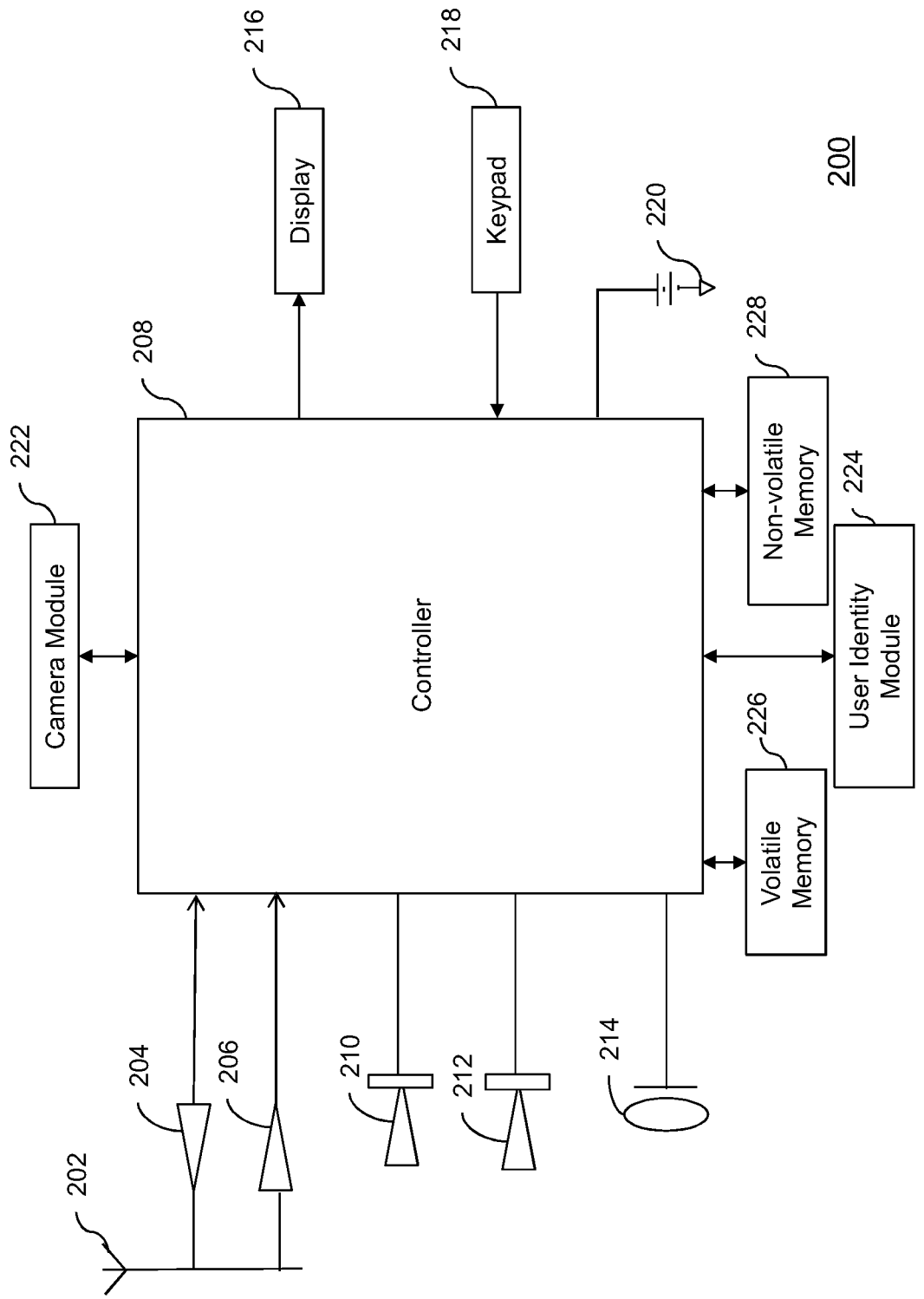
FIG. 2 illustrates a device in accordance with an example embodiment.

FIG. 2 illustrates a device 200 in accordance with an example embodiment. In an embodiment, the device 200 may be an example of the device 108 (refer to FIG. 1). It should be understood, however, that the device 200 as illustrated and hereinafter described is merely illustrative of one type of device that may benefit from various embodiments, therefore, should not be taken to limit the scope of the embodiments. As such, it should be appreciated that at least some of the components described below in connection with the device 200 may be optional and thus in an example embodiment may include more, less or different components than those described in connection with the example embodiment of FIG. 2. The device 200 could be any of a number of types of mobile electronic devices, for example, portable digital assistants (PDAs), pagers, mobile televisions, gaming devices, cellular phones, all types of computers (for example, laptops, mobile computers or desktops), cameras, audio/video players, radios, global positioning system (GPS) devices, media players, mobile digital assistants, or any combination of the aforementioned, and other types of communications devices.

The device 200 may include an antenna 202 (or multiple antennas) in operable communication with a transmitter 204 and a receiver 206. The device 200 may further include an apparatus, such as a controller 208 or other processing device that provides signals to and receives signals from the transmitter 204 and receiver 206, respectively. The signals may include signaling information in accordance with the air interface standard of the applicable cellular system, and/or may also include data corresponding to user speech, received data and/or user generated data. In this regard, the device 200 may be capable of operating with one or more air interface standards, communication protocols, modulation types, and access types. By way of illustration, the device 200 may be capable of operating in accordance with any of a number of first, second, third and/or fourth-generation communication protocols or the like. For example, the device 200 may be capable of operating in accordance with second-generation (2G) wireless communication protocols IS-136 (time division multiple access (TDMA)), GSM (global system for mobile communication), and IS-95 (code division multiple access (CDMA)), or with third-generation (3G) wireless communication protocols, such as Universal Mobile Telecommunications System (UMTS), CDMA1000, wideband CDMA (WCDMA) and time division-synchronous CDMA (TD-SCDMA), with 3.9G wireless communication protocol such as evolved-universal terrestrial radio access network (E-UTRAN), with fourth-generation (4G) wireless communication protocols, or the like. As an alternative (or additionally), the device 200 may be capable of operating in accordance with non-cellular communication mechanisms. For example, computer networks such as the Internet, local area network, wide area networks, and the like; short range wireless communication networks such as Bluetooth® networks, Zigbee® networks, Institute of Electric and Electronic Engineers (IEEE) 802.11x networks, and the like; wireline telecommunication networks such as public switched telephone network (PSTN).

The controller 208 may include circuitry implementing, among others, audio and logic functions of the device 200. For example, the controller 208 may include, but are not limited to, one or more digital signal processor devices, one or more microprocessor devices, one or more processor(s) with accompanying digital signal processor(s), one or more processor(s) without accompanying digital signal processor(s), one or more special-purpose computer chips, one or more field-programmable gate arrays (FPGAs), one or more controllers, one or more application-specific integrated circuits (ASICs), one or more computer(s), various analog to digital converters, digital to analog converters, and/or other support circuits. Control and signal processing functions of the device 200 are allocated between these devices according to their respective capabilities. The controller 208 thus may also include the functionality to convolutionally encode and interleave message and data prior to modulation and transmission. The controller 208 may additionally include an internal voice coder, and may include an internal data modem. Further, the controller 208 may include functionality to operate one or more software programs, which may be stored in a memory. For example, the controller 208 may be capable of operating a connectivity program, such as a conventional Web browser. The connectivity program may then allow the device 200 to transmit and receive Web content, such as location-based content and/or other web page content, according to a Wireless Application Protocol (WAP), Hypertext Transfer Protocol (HTTP) and/or the like. In an example embodiment, the controller 108 may be embodied as a multi-core processor such as a dual or quad core processor. However, any number of processors may be included in the controller 108.

The device 200 may also comprise a user interface including an output device such as a ringer 210, an earphone or speaker 212, a microphone 214, a display 216, and a user input interface, which may be coupled to the controller 208. The user input interface, which allows the device 200 to receive data, may include any of a number of devices allowing the device 200 to receive data, such as a keypad 218, a touch display, a microphone or other input device. In embodiments including the keypad 218, the keypad 218 may include numeric (0-9) and related keys (#, *), and other hard and soft keys used for operating the device 200. Alternatively or additionally, the keypad 218 may include a conventional QWERTY keypad arrangement. The keypad 218 may also include various soft keys with associated functions. In addition, or alternatively, the device 200 may include an interface device such as a joystick or other user input interface. The device 200 further includes a battery 220, such as a vibrating battery pack, for powering various circuits that are used to operate the device 200, as well as optionally providing mechanical vibration as a detectable output.

In an example embodiment, the device 200 includes a media capturing element, such as a camera, video and/or audio module, in communication with the controller 108. The media capturing element may be any means for capturing an image, video and/or audio for storage, display or transmission. In an example embodiment, the media capturing element is a camera module 222 which may include a digital camera capable of forming a digital image file from a captured image. As such, the camera module 222 includes all hardware, such as a lens or other optical component(s), and software for creating a digital image file from a captured image. Alternatively, or additionally, the camera module 222 may include the hardware needed to view an image, while a memory device of the device 100 stores instructions for execution by the controller 208 in the form of software to create a digital image file from a captured image. In an example embodiment, the camera module 222 may further include a processing element such as a co-processor, which assists the controller 208 in processing image data and an encoder and/or decoder for compressing and/or decompressing image data. The encoder and/or decoder may encode and/or decode according to a JPEG standard format or another like format. For video, the encoder and/or decoder may employ any of a plurality of standard formats such as, for example, standards associated with H.261, H.262/MPEG-2, H.263, H.264, H.264/MPEG-4, MPEG-4, and the like. In some cases, the camera module 222 may provide live image data to the display 216. In an example embodiment, the display 216 may be located on one side of the device 200 and the camera module 222 may include a lens positioned on the opposite side of the device 200 with respect to the display 216 to enable the camera module 222 to capture images on one side of the device 200 and present a view of such images to the user positioned on the other side of the device 200.

The device 200 may further include a user identity module (UIM) 224. The UIM 224 may be a memory device having a processor built in. The UIM 224 may include, for example, a subscriber identity module (SIM), a universal integrated circuit card (UICC), a universal subscriber identity module (USIM), a removable user identity module (R-UIM), or any other smart card. The UIM 224 typically stores information elements related to a mobile subscriber. In addition to the UIM 224, the device 200 may be equipped with memory. For example, the device 200 may include volatile memory 226, such as volatile random access memory (RAM) including a cache area for the temporary storage of data. The device 200 may also include other non-volatile memory 228, which may be embedded and/or may be removable. The non-volatile memory 228 may additionally or alternatively comprise an electrically erasable programmable read only memory (EEPROM), flash memory, hard drive, or the like. The memories may store any number of pieces of information, and data, used by the device 200 to implement the functions of the device 200.

Figure 3:
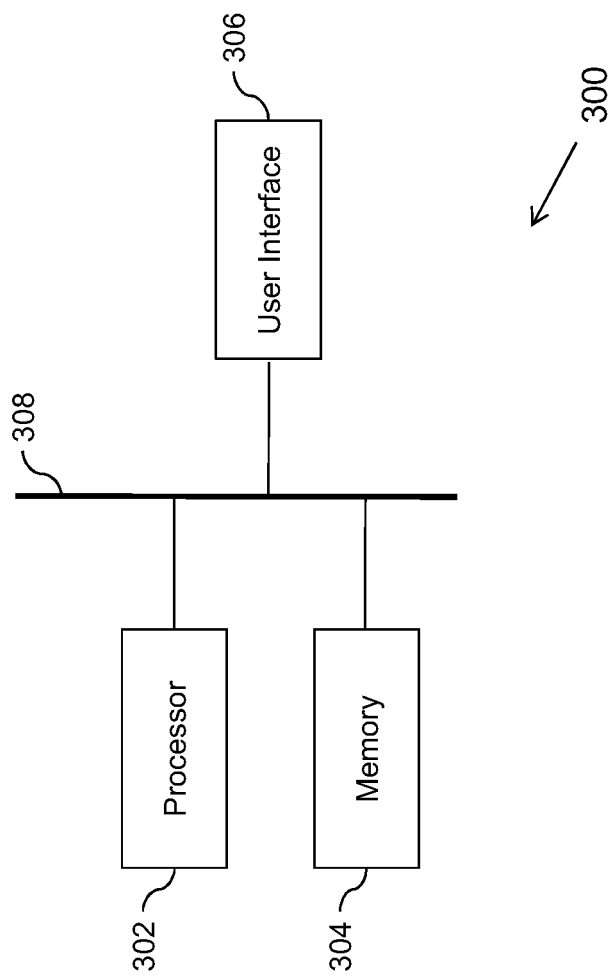
FIG. 3 illustrates an apparatus for activity recognition in accordance with an example embodiment.

FIG. 3 illustrates an apparatus 300 for activity recognition, in accordance with an example embodiment. The apparatus 300 for activity recognition may be employed, for example, in the device 200 of FIG. 2. However, it should be noted that the apparatus 300, may also be employed on a variety of other devices both mobile and fixed, and therefore, embodiments should not be limited to application on devices such as the device 200 of FIG. 2. Alternatively, embodiments may be employed on a combination of devices including, for example, those listed above. Various embodiments may be embodied wholly at a single device, (for example, the device 200). It should also be noted that some of the devices or elements described below may not be mandatory and thus some may be omitted in certain embodiments.

In an embodiment, the apparatus 300 includes or otherwise is in communication with at least one processor 302 and at least one memory 304. Examples of the at least one memory 304 include, but are not limited to, volatile and/or non-volatile memories. Some examples of the volatile memory include, but are not limited to, random access memory, dynamic random access memory, static random access memory, and the like. Some example of the non-volatile memory includes, but are not limited to, hard disks, magnetic tapes, optical disks, programmable read only memory, erasable programmable read only memory, electrically erasable programmable read only memory, flash memory, and the like. The memory 304 may be configured to store information, data, applications, instructions or the like for enabling the apparatus 300 to carry out various functions in accordance with various example embodiments. For example, the memory 304 may be configured to buffer a sampling information comprising a basis information and a selection information for processing by the processor 302. Additionally or alternatively, the memory 304 may be configured to store instructions for execution by the processor 302.

An example of the processor 302 may include the controller 308. The processor 302 may be embodied in a number of different ways. The processor 302 may be embodied as a multi-core processor, a single core processor; or combination of multi-core processors and single core processors. For example, the processor 302 may be embodied as one or more of various processing means such as a coprocessor, a microprocessor, a controller, a digital signal processor (DSP), processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like. In an example embodiment, the multi-core processor may be configured to execute instructions stored in the memory 304 or otherwise accessible to the processor 302. Alternatively or additionally, the processor 302 may be configured to execute hard coded functionality. As such, whether configured by hardware or software methods, or by a combination thereof, the processor 302 may represent an entity, for example, physically embodied in circuitry, capable of performing operations according to various embodiments while configured accordingly. For example, if the processor 302 is embodied as two or more of an ASIC, FPGA or the like, the processor 302 may be specifically configured hardware for conducting the operations described herein. Alternatively, as another example, if the processor 302 is embodied as an executor of software instructions, the instructions may specifically configure the processor 302 to perform the algorithms and/or operations described herein when the instructions are executed. However, in some cases, the processor 302 may be a processor of a specific device, for example, a mobile terminal or network device adapted for employing embodiments by further configuration of the processor 302 by instructions for performing the algorithms and/or operations described herein. The processor 302 may include, among other things, a clock, an arithmetic logic unit (ALU) and logic gates configured to support operation of the processor 302.

A user interface 306 may be in communication with the processor 302. Examples of the user interface 306 include, but are not limited to, input interface and/or output user interface. The input interface is configured to receive an indication of a user input. The output user interface provides an audible, visual, mechanical or other output and/or feedback to the user. Examples of the input interface may include, but are not limited to, a keyboard, a mouse, a joystick, a keypad, a touch screen, soft keys, and the like. Examples of the output interface may include, but are not limited to, a display such as light emitting diode display, thin-film transistor (TFT) display, liquid crystal displays, active-matrix organic light-emitting diode (AMOLED) display, a microphone, a speaker, ringers, vibrators, and the like. In an example embodiment, the user interface 306 may include, among other devices or elements, any or all of a speaker, a microphone, a display, and a keyboard, touch screen, or the like. In this regard, for example, the processor 302 may comprise user interface circuitry configured to control at least some functions of one or more elements of the user interface 306, such as, for example, a speaker, ringer, microphone, display, and/or the like. The processor 302 and/or user interface circuitry comprising the processor 302 may be configured to control one or more functions of one or more elements of the user interface 306 through computer program instructions, for example, software and/or firmware, stored on a memory, for example, the at least one memory 304, and/or the like, accessible to the processor 302.

In an example embodiment, the apparatus 300 may include an electronic device. Some examples of the electronic device include communication device, media capturing device, media capturing device with communication capabilities, computing devices, and the like. Some examples of the communication device may include a mobile phone, a personal digital assistant (PDA), and the like. Some examples of computing device may include a laptop, a personal computer, and the like. In an example embodiment, the electronic device may include a user interface, for example, the UI 206, having user interface circuitry and user interface software configured to facilitate a user to control at least one function of the electronic device through use of a display and further configured to respond to user inputs. In an example embodiment, the electronic device may include a display circuitry configured to display at least a portion of the user interface of the electronic device. The display and display circuitry may be configured to facilitate the user to control at least one function of the electronic device.

In an example embodiment, the electronic device may be embodied as to include a transceiver. The transceiver may be any device operating or circuitry operating in accordance with software or otherwise embodied in hardware or a combination of hardware and software. For example, the processor 302 operating under software control, or the processor 302 embodied as an ASIC or FPGA specifically configured to perform the operations described herein, or a combination thereof, thereby configures the apparatus or circuitry to perform the functions of the transceiver. The transceiver may be configured to receive a sampled data from one or more sensors.

These components (302-306) may communicate with each other via a centralized circuit system 308. The centralized circuit system 308 may be configured to, among other things, provide or enable communication between the components (302-306) of the apparatus 300. In certain embodiments, the centralized circuit system 308 may be a central printed circuit board (PCB) such as a motherboard, main board, system board, or logic board. The centralized circuit system 308 may also, or alternatively, include other printed circuit assemblies (PCAs) or communication channel media.

In an example embodiment, the processor 302 is configured to, with the content of the memory 304, and optionally with other components described herein, to cause the apparatus 300 to perform activity recognition for an activity. In an example embodiment, the activity may be a human activity. For example, the activity may be walking, jogging, running, climbing-up, climbing down, and the like. Various other real-world activities may be recognized by the apparatus 300 without limiting the scope of the disclosure.

In an example embodiment, the processor 302 is configured to, with the content of the memory 304, and optionally with other components described herein, to cause the apparatus 300 to generate a basis matrix associated with a space. In an embodiment, the basis matrix may be a complete basis matrix. The complete basis matrix may be configured to span an entire space, such that, any vector on the space can be written as a linear combination of the n vectors of the basis. In an embodiment, the size of the complete basis matrix may be adjustable. In an embodiment, the basis matrix may be generated by a random number generator providing random numbers evenly distributed in the interval [−1, 1]. In order to make a set of n vectors into a complete basis, the randomly generated vectors may be orthonormalised. In an example embodiment, the orthonormal random matrix may be generated based on a QR decomposition method, wherein a matrix is decomposed into a product of an orthogonal matrix (Q) and an upper triangular matrix (R).

In an example embodiment, the randomly generated vectors may be orthonormalised based on a Gram-Schmidt algorithm. This basis corresponds to an orthonormal square matrix. In an embodiment, a processing means may be configured to generate the matrix of complete basis. An example of the processing means may include the processor 302, which may be an example of the controller 208.

In an example embodiment, the processor 302 is configured to, with the content of the memory 304, and optionally with other components described herein, to cause the apparatus 300 to send a sampling information to the one or more sensors for facilitating the one or more sensors to generate the sampled data. In an embodiment, the sampling information includes the basis matrix and a selection information for selecting a subset of the basis matrix. The subset of the basis matrix may include a set of basis vectors that may be utilized by the one or more sensors for generating the sampled data. In an embodiment, a processing means may be configured to send the sampling information to the one or more sensors. An example of the processing means may include the processor 302, which may be an example of the controller 208. In an embodiment, the sampling information may be sent to the one or more sensors over a wireless link.

In an embodiment, the one or more sensors may be configured to receive the basis matrix and process the activity data based on the basis matrix and the selection information. Based on the processing of the activity data, the one or more sensors may be configured to generate a sampled data. In an embodiment, the sampled data may be generated based on compressive sampling of the activity data. The description and functionality of the one or more sensors for generating the sampled data is explained further with reference to FIGS. 4 and 5.

In an example embodiment, the processor 302 is configured to, with the content of the memory 304, and optionally with other components described herein, to cause the apparatus 300 to receive the sampled data associated with the activity from the one or more sensors. In an embodiment, the apparatus 300 is configured to receive the sampled data until a frame of the sampled data is received. In an embodiment, the size of the frame may be about 0.1 s-10 s. In an embodiment, if multiple sensors are sending a respective sampled data to the apparatus 300, then the sampled data received from multiple sensors may be arranged in a sequence of their respective reception at the apparatus 300. The arrangement of the sampled data received from the one or more sensors is explained in further detail with reference to FIG. 6.

In an embodiment, the apparatus 300 is configured to classify the activity based on the sampled data sent by the one or more sensors. In an embodiment, the processor 302 is configured to, with the content of the memory 304, and optionally with other components described herein, to cause the apparatus 300 to apply a classification rule to the sampled data. In an embodiment, the classification rule/model for supervised learning may be trained by utilizing a labeled activity data. In an embodiment, the labeled activity data may be produced based on the sampling information that is utilized in the performing random projection. In an embodiment, the training set with labels may be represented in the basis that is utilized for sampling of the activity data at the one or more sensors. In an embodiment, the classification rule may utilize one of a quadratic discriminant mechanism, support vector machine, decision tree, neural net and a Boltzmann machine mechanisms for labeling the activity data.

In another embodiment, the labels in the training set may be provided initially (e.g. as in "factory settings") in a basis so that it may be convenient to compute the training set in any undercomplete basis, for example, the labels utilized for compressive sampling of the activity data. In another embodiment, the labels associated with the training set may be deduced from other data. For instance, the labels may be available for partial activity data when the activity data is sampled in a complete basis. The labels may be used to generate a training set of undercomplete (projected) data with additional sensors included. In yet another embodiment, the labels may be obtained based on an unsupervised learning. For example, various identify clusters (e.g. k-means algorithm) may be generated and labels may be obtained by "asking" information from the user. For instance, in response to detection of a motion activity, a query such as 'were you running?' may be asked.

In an embodiment, a processing means may be configured to classify the activity based on the sampled data and the classification rule. An example of the processing means may include the processor 302, which may be an example of the controller 208. The classification of the activity data may provide an activity class (e.g. running, sitting, walking, etc.) as output. It will be understood herein that instead of decompressing the sampled data, the sampled data may be directly utilized for the purpose of classification. An advantage of utilizing the sampled data directly (without decompression) is that the computational power associated with decompression of data is reduced.

In an example embodiment, the processor 302 is configured to, with the content of the memory 304, and optionally with other components described herein, to cause the apparatus 300 to store a first label into which the activity is classified. In an embodiment, a memory means may be configured to store the first label. An example of the processing means may include the memory means 304, which may be an example of the non-volatile memory 228.

In an embodiment, the output of the classification may contain error due to the presence of noise in the measurement of activity data when the activity data is acquired by the one or more sensors. In an embodiment, the error in the sampled data may lead to classification of the activity into an incorrect label. In an embodiment, the processor 302 is configured to, with the content of the memory 304, and optionally with other components described herein, to cause the apparatus 300 to determine the error associated with the classification of the activity data. In an embodiment, since the activities performed by the users do not undergo substantial fluctuation over a very short time scale (for example, seconds), a variance in the output of the classification output may be utilized for detection of any errors in the classification. In an embodiment, a processing means may be configured to determine the error associated with the sampled data. An example of the processing means may include the processor 302, which may be an example of the controller 208.

In an embodiment, the processor 302 is configured to, with the content of the memory 304, and optionally with other components described herein, to cause the apparatus 300 to apply error correction on the output of the classification. In an example embodiment, an error correction mechanism may include majority voting. It will be understood that certain other complex correlations may also be utilized for applying error correction to the classification output. In an embodiment, the processor 302 is configured to, with the content of the memory 304, and optionally with other components described herein, to cause the apparatus 300 to compare the error in the sampled data with a threshold error. In an embodiment, the processor 302 is configured to, with the content of the memory 304, and optionally with other components described herein, to cause the apparatus 300 to update or retain the sampling information based on a comparison of the error with a threshold error. In an embodiment, the threshold error may be preset in the apparatus 300.

In an embodiment, the processor 302 is configured to, with the content of the memory 304, and optionally with other components described herein, to cause the apparatus 300 to retain the sampling information by retaining values of the number of basis vectors and the basis size associated with the selection information on determination of the error to be lower than the threshold error.

In an embodiment, the processor 302 is configured to, with the content of the memory 304, and optionally with other components described herein, to cause the apparatus 300 to update the sampling information by increasing the number of basis vectors associated with the subset of the complete basis matrix upon determination of the error to be greater than the threshold error.

In an embodiment, the processor 302 is configured to, with the content of the memory 304, and optionally with other components described herein, to cause the apparatus 300 to update the sampling information by increasing the basis size associated with the subset of the complete basis matrix upon determination of the error to be greater than or equal to the threshold error during a threshold number of updating of the basis size. In an embodiment, the processor 302 is configured to, with the content of the memory 304, and optionally with other components described herein, to cause the apparatus 300 to update the sampling information by reducing values of the number of basis vectors and the basis size associated with the selection information on determination of the error to be lesser than the threshold error.

In an example embodiment, the processor 302 is configured to, with the content of the memory 304, and optionally with other components described herein, to cause the apparatus 300 to reclassify the activity on determination of the error to be greater than or equal to the threshold error. In an embodiment, the activity may be reclassified by utilizing the updated sampling information. In an example embodiment, a processing means may be configured to update or retain the sampling information based on a comparison of the error with a threshold error. An example of the processing means may include the processor 302, which may be an example of the controller 208.

Figure 4:
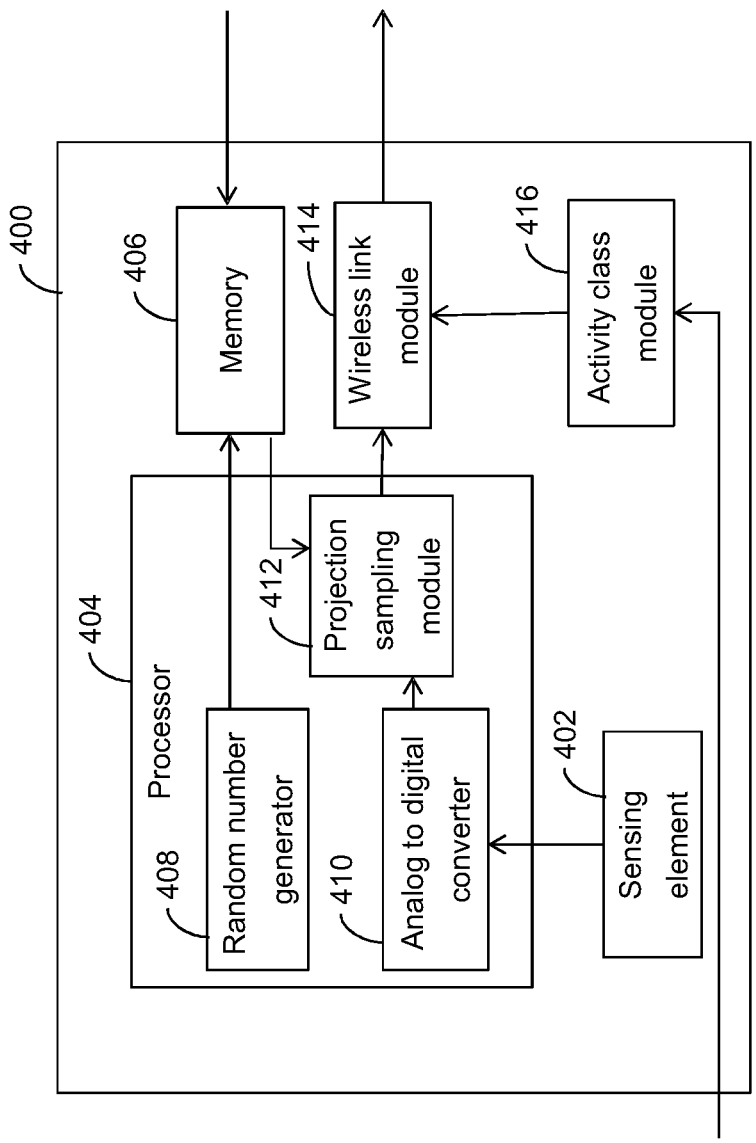
FIG. 4 illustrates another apparatus for activity recognition in accordance with another example embodiment.

FIG. 4 illustrates an apparatus 400 for activity recognition, in accordance with an example embodiment. The apparatus 400 for activity recognition may be employed, in a device that is configured to sense activity of a user. For example, the apparatus 400 may be employed in a variety of sensors. In an example embodiment, the apparatus 400 may be employed in wearable sensors that may be attached to a user's body to measure attributes of interest such as motion, location, temperature, electrocardiogram (ECG), and the like. Various embodiments may be embodied wholly at a single device or a combination of devices. It should also be noted that some of the devices or elements described below may not be mandatory and thus some may be omitted in certain embodiments.

In an embodiment, the apparatus 400 includes or otherwise is in communication with at least one processor 404 and at least one memory 406. Examples of the at least one memory 406 include, but are not limited to, volatile and/or non-volatile memories. Some examples of the volatile memory include, but are not limited to, random access memory, dynamic random access memory, static random access memory, and the like. Some example of the non-volatile memory includes, but not limited to, hard disks, magnetic tapes, optical disks, programmable read only memory, erasable programmable read only memory, electrically erasable programmable read only memory, flash memory, and the like. The memory 406 may be configured to store information, data, applications, instructions or the like for enabling the apparatus 400 to carry out various functions in accordance with various example embodiments. For example, the memory 406 may be configured to buffer input data comprising a sampling information for processing by the processor 404. Additionally or alternatively, the memory 406 may be configured to store instructions for execution by the processor 404.

The processor 404 may be embodied in a number of different ways. The processor 302 may be embodied as a multi-core processor, a single core processor; or combination of multi-core processors and single core processors. For example, the processor 404 may be embodied as one or more of various processing means such as a coprocessor, a microprocessor, a controller, a digital signal processor (DSP), processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like. In an example embodiment, the multi-core processor may be configured to execute instructions stored in the memory 406 or otherwise accessible to the processor 404. Alternatively or additionally, the processor 404 may be configured to execute hard coded functionality. As such, whether configured by hardware or software methods, or by a combination thereof, the processor 404 may represent an entity, for example, physically embodied in circuitry, capable of performing operations according to various embodiments while configured accordingly. For example, if the processor 404 is embodied as two or more of an ASIC, FPGA or the like, the processor 404 may be specifically configured hardware for conducting the operations described herein. Alternatively, as another example, if the processor 404 is embodied as an executor of software instructions, the instructions may specifically configure the processor 404 to perform the algorithms and/or operations described herein when the instructions are executed. However, in some cases, the processor 404 may be a processor of a specific device, for example, a mobile terminal or network device adapted for employing embodiments by further configuration of the processor 404 by instructions for performing the algorithms and/or operations described herein. The processor 404 may include, among other things, a clock, an arithmetic logic unit (ALU) and logic gates configured to support operation of the processor 404.

In an embodiment, one or more sensors employing the apparatus 400 may be configured to sense human activity. In an embodiment, in addition to the processor 404 and memory 406, the apparatus 400 may include a sensing element 402, a wireless link module 4141, and an activity class module 416. In an embodiment, the processor may further include an analog to digital converter 410, a random number generator 408 and a projection sampling module 412. In an embodiment, the sensing element 402 is configured to sense the activity. In embodiment, the A/D converter 410 is coupled with the sensing element 402, and is configured to perform an analog to digital conversion of the activity data sensed by the sensing element 402. In an embodiment, an output of the A/D converter 410 may be utilized for performing sampling of the activity data. In an embodiment, the output of the A/D converter may be stored in a memory, for example the memory 406 of the apparatus 400. In an embodiment, the output of the A/D converter 410 may be stored in the memory 406 until a data vector associated with the activity data of length N is obtained.

As discussed above, the activity data may be converted from analog domain to digital domain for performing random sampling. Alternately, random sampling may be performed in the analog domain, for example, by using programmable amplifier and an integrator circuit.

In an embodiment, the processor 404 is configured to, with the content of the memory 406, and optionally with other components described herein, to cause the apparatus 400 to performing random sampling of the activity data based on a sampling information sent by a device, for example, the device 200 (explained with reference to FIG. 2). In an embodiment, the processor 404 is configured to, with the content of the memory 406, and optionally with other components described herein, to cause the apparatus 400 to receive a sampling information from the apparatus 300. In an embodiment, the sampling information includes a basis matrix and a selection information for selecting at least a subset of the basis matrix. In an embodiment, the subset of basis matrix may include a set of randomly selected basis vectors along which the activity data may be sampled to generate the sampled data. In an embodiment, the basis matrix may be a complete basis matrix wherein the basis vectors may span an entire predefined space as opposed to a subspace of the predefined subspace. In an embodiment, the complete basis matrix associated with the sampling information may be an N×N matrix. In an embodiment, a processing means may be configured to receive a sampling information from the apparatus 300. An example of the processing means may include the processor 404.

In an embodiment, the processor 404 is further configured to, with the content of the memory 406, and optionally with other components described herein, to cause the apparatus 400 to store the sampling information received from the apparatus 300. In an embodiment, a memory means may be configured to store the sampling information received from the apparatus 300. An example of the memory means may include the memory 406.

In an embodiment, the processor 404 is configured to, with the content of the memory 406, and optionally with other components described herein, to cause the apparatus 400 to perform compressive sampling of an activity data associated with the activity based at least on the sampling information and a sampling criteria to generate a sampled data associated with the activity. In an embodiment, the sampling criteria includes selection of an incoherent basis for performing compressive sampling of the activity data.

In an embodiment, the processor 404 is configured to, with the content of the memory 406, and optionally with other components described herein, to cause the apparatus 400 to select the subset of the basis matrix based on the selection information. For example, a subset of M basis vectors may be randomly selected from the basis matrix (of size N×N) to form an M×N sampling matrix. The M×N sampling matrix may be denoted by 'A'. In an example embodiment, a processing means may be configured to randomly select the set of basis vectors based on the sampling information. An example of the processing means may include processing means, for example a random number generator 408.

In an embodiment, the processor 404 is configured to, with the content of the memory 406, and optionally with other components described herein, to cause the apparatus 400 to compressively sample the activity data along the set of randomly selected basis vectors and in response generate a sampled data. In an example embodiment, for sampling the activity data along the set of basis vectors, the processor 404 is configured to, with the content of the memory 406, and optionally with other components described herein, to cause the apparatus 400 to multiply the data vector (x) with a sampling matrix A to obtain a sample vector (y) of length M. In an embodiment, a processing means may be configured to multiply the data vector with the sampling matrix A to obtain the sample vector of length M. An example of the processing means may include a projection sampling module 412. The sampled data may be generated based on the expression:

$$y = A^T x,$$

where, A denotes the N×M sampling matrix whose columns are the (orthogonal) basis vectors, and x denotes the N dimensional uncompressed data vector In an embodiment, the processor 404 is configured to, with the content of the memory 406, and optionally with other components described herein, to cause the apparatus 400 to send the sampled data to the apparatus (for example the apparatus 300) for facilitating labeling of the activity. In an embodiment, the apparatus 400 may send the sampled data to the apparatus 300 until a frame of the sampled data may be sent to the apparatus 300. In an example embodiment, the frame size may be about 0.1 s-10 s. In an embodiment, the sampled data may be sent to the apparatus 300 through the wireless link module 414.

In an embodiment, the apparatus 400 may send the sampled data to the apparatus 300. A mode of operation of the apparatus 400 wherein the apparatus is configured to send only the sampled data may be referred to as 'unlabeled mode'. In another embodiment, the apparatus 400 may send a user-selected label to the apparatus 300. In an embodiment, the apparatus 400 may include a user interface for receiving a user input associated with the label from the user. For example, the user may input the label by utilizing the activity class module 416. The activity class module 416 may be coupled with the wireless link module 414 for facilitating sending of the activity class provided by the user to the apparatus 200. As disclosed herein, a mode of operation of the apparatus 400 wherein the apparatus is configured to send a label along with the sampled data to the device 300 may be referred to as 'labeled mode'.

As already discussed with reference to FIG. 3, the apparatus 300 may utilize the sampled data for classifying the label to be assigned to the activity. Additionally, the apparatus 300 may determine an error in the sampled data. In an embodiment, when the error in the sampled data is determined to be greater than a threshold error, then the apparatus 300 is configured to update the selection information and resend the updated selection information to the apparatus 400.

In an embodiment, the processor 404 is configured to, with the content of the memory 406, and optionally with other components described herein, to cause the apparatus 400 to receive the updated sampling information from the apparatus 300. In an embodiment, the processor 404 is configured to, with the content of the memory 406, and optionally with other components described herein, to cause the apparatus 400 to perform compressive sampling of the activity data based at least on the updated selection information to generate an updated sampled data. In an embodiment, the updated sampled data may be generated in a manner similar to the generation of the sampled data. In an embodiment, the processor 404 is configured to, with the content of the memory 406, and optionally with other components described herein, to cause the apparatus 400 to send the updated sampled data to the apparatus 300 for facilitating relabeling of the activity. In an embodiment, the wireless link module 410 may be configured to send the updated sampled data to the apparatus 300.

As already discussed, in an embodiment, apparatus 400 may include the sensing element 402, the processor 404, the memory 406, the wireless link module 414 and the activity class module 416. In an embodiment, the processor 404 may include the A/D converter 410, the random number generator 408, and the projection sampling module 412. In an alternate embodiment, instead of separate modules mentioned above, the apparatus 400 may include an integrated hardware solution implementing the modules for A/D converter, sensing element, random number generator, and projection sampling module, thereby precluding the need of separate modules. For example, the apparatus 400 may include smart sensors in which analog or mixed signal circuitry are combined with the sensor readout electronics.

FIG. 5 illustrates an example of compressive sampling of an activity data for activity recognition, in accordance with an example embodiment. In an example embodiment, for performing compressive sampling, an analog to digital conversion of an activity data 502 is performed and a data vector 504 associated the activity data 502 is generated. In an embodiment, the data vector 504 may be sampled along randomly selected basis vectors.

In an embodiment, a data vector such as a data vector 504 of length N (e.g. in time domain) may be projected along a set of basis vectors (for example basis vectors 506, 508). In an embodiment, the set of basis vectors may be randomly selected based on a sampling information received from the apparatus 300. In another embodiment, the set of basis vectors may be selected randomly and orthonormalised. In an example embodiment, the set of basis vectors may be orthonormalised based on a Gram-Schmidt procedure.

In an example embodiment illustrated in FIG. 5, the set of randomly selected basis vectors 506, 508 associated with the sampling matrix may be multiplied with the data vector 504 to obtain samples such as samples, 510, 512. Let x denote the N dimensional uncompressed data vector and let A denote an N by M sampling matrix whose columns are the (orthogonal) basis vectors. Then, the sampled data is an M dimensional vector y such that:

$$y = A^T x.$$

In an example embodiment, the basis vectors such as basis vectors 506, 508 may include various non-zero real valued entries. In such a scenario, the samples may be obtained by summing up the components. In an example embodiment, column vectors may be utilized as sampling vectors.

FIG. 6 illustrates a sequence of transmission of sampled data in accordance with an embodiment. As previously discussed, the sampled data 610 (represented by y) may be transmitted or sent to the apparatus 300 for facilitating learning and activity recognition. In an embodiment, activity recognition may be performed based on the sampled data received from multiple sensors that may be configured to sense different quantities at different sampling rates. For example, sensors employed in an accelerometer and compass may facilitate in sensing of accelerometer data and compass orientation data, respectively. The accelerometer data and the compass orientation data may be sensed and subsequently sampled by different sensors. In an embodiment, the activity data received from multiple vectors $y_i$ (for example, 612, 614, 616, 618) may generate a data set that may be represented as:

$$\{y_i, i=1, \ldots, M\}$$

In an embodiment, the activity data received from the multiple sensors may be arranged into a vector prior to performing random projection. For example, the data associated with the data set 610 may be arranged in a vector 620 prior to performing random projection of the activity data. For example, as illustrated in FIG. 6, the data from the vectors 612, 614, 616 may be received and stored at location 622, 624, 626 respectively of the vector 620. In an embodiment, the data may be arranged in a vector 620 in a sequential manner, i.e. in sequence of receiving of the data from the respective sensor at the apparatus 300.

FIG. 7 is a flowchart depicting an example method 700 for activity recognition, in accordance with an example embodiment. The method 700 depicted in the flow chart may be executed by, for example, the apparatus 300 of FIG. 3. In an embodiment, the method may be executed by a device that may be communicatively coupled to one or more sensors. In an embodiment, the device may be a mobile phone, a PDA, a laptop and the like.

In an embodiment, the apparatus 300 may be configured to recognize an "activity" being performed by a user based on a sampled data received from one or more sensor. In an embodiment, the activity may include walking, jogging, running, and any other motion or movement phenomenon being performed by the user. In an embodiment, the activity may be sensed by the one or more sensors. For example, the one or more sensors may capture an activity data associated with the activity, and process the activity data to generate sampled data. In an embodiment, the sampled data may be generated by the one or more sensors based on a sampling information that may be sent by the apparatus 300 to the one or more sensors. In an embodiment, the sampling information includes a basis matrix and a selection information for selecting at least a subset of the basis matrix. In an embodiment, the basis matrix may be a complete basis matrix wherein the basis vectors may span an entire predefined space as opposed to a subspace of the predefined subspace.

At block 702, the method 700 includes receiving the sampled data associated with the activity at the apparatus 300 from the one or more sensors. In an embodiment, the sampled data may be sent to the apparatus 300 by one or more devices embodying the apparatus 400 (explained in FIG. 4). In an embodiment, examples of the device embodying the apparatus 400 may include sensors such as an accelerometer, a barometer, a compass, and the like. At block 704, the activity may be classified based at least on the sampled data. In an embodiment, classifying the activity may include assigning a label to the activity. In an embodiment, the activity may be classified based on a classification rule or model. For example, the sampled data may be classified based on a quadratic discriminant analysis. In another embodiment, the sampled data may be classified based on the classification rule as well as a user input. In an embodiment, the user input may be sent by the one or more sensors.

In an embodiment, the sampled data received at the device may include error due to noise associated with the one or more sensors. In an embodiment, the error in the sampled data may lead to a wrong classification of the activity. At block 706, an error in the classification of the activity may be determined. In an embodiment, a variance in an output of the classification of the activity may be utilized as a measure for error determination since user activities may remain substantially same (i.e. do not fluctuate) over a very short time scale (seconds). Accordingly, at different time instances during this short time interval, the sampled data may be computed a threshold number of times, and classified by assigning a label thereto. In case, a variation in the classification of activity is detected during the classification, the classification of the activity may be regarded as incorrect.

In an embodiment, the error in the classification may be computed and compared with a threshold error. In an embodiment, the threshold error may be preset in the apparatus 400. In an embodiment, based on a comparison of the error with the threshold error, the sampling information may be updated or retained at block 708. For example, on detection of absence of any errors in classification, the number of vectors associated with the sampling information may be retained or reduced. In an embodiment, the size of the sampling matrix may be reduced by reducing the number of vectors therein. In an alternate embodiment, the size of the sampling matrix may be retained as such if the size of the sampling matrix is determined to be already at a minimum allowable size. In an embodiment, the minimum allowable size of the matrix may be preset in the apparatus 400.

In an embodiment, on determination of error being greater than or equal to the threshold, an error correction may be applied to the sampled data. Examples of error correction methods includes, but are not limited to majority voting, and the like. In an example embodiment, on determination of error being greater than or equal to the threshold error, the sampling information may be updated. For example, based on the determined error to be greater than the threshold error, the number of basis vectors may be increased. Additionally or optionally, if the error in the classification performed during previous predetermined number of times is determined to be greater than the threshold error, then the size of the complete basis matrix associated with the sampling information may be increased. For example, if the error is determined to be greater than or equal to the threshold error during last ten classifications, then the size of the complete basis matrix may be increased.

In an example embodiment, a processing means may be configured to perform some or all of: receiving, at a device, a sampled data associated with an activity from one or more sensors wirelessly coupled to the device, the sampled data being generated at the one or more sensors based on a compressive sampling of an activity data associated with the activity, the compressive sampling being performed based on a sampling information; classifying the activity based at least on the sampled data; determining an error associated with the classification of the activity; and updating the sampling information based on a comparison of the error with a threshold error. An example of the processing means may include the processor 302, which may be an example of the controller 208.

Figure 8:
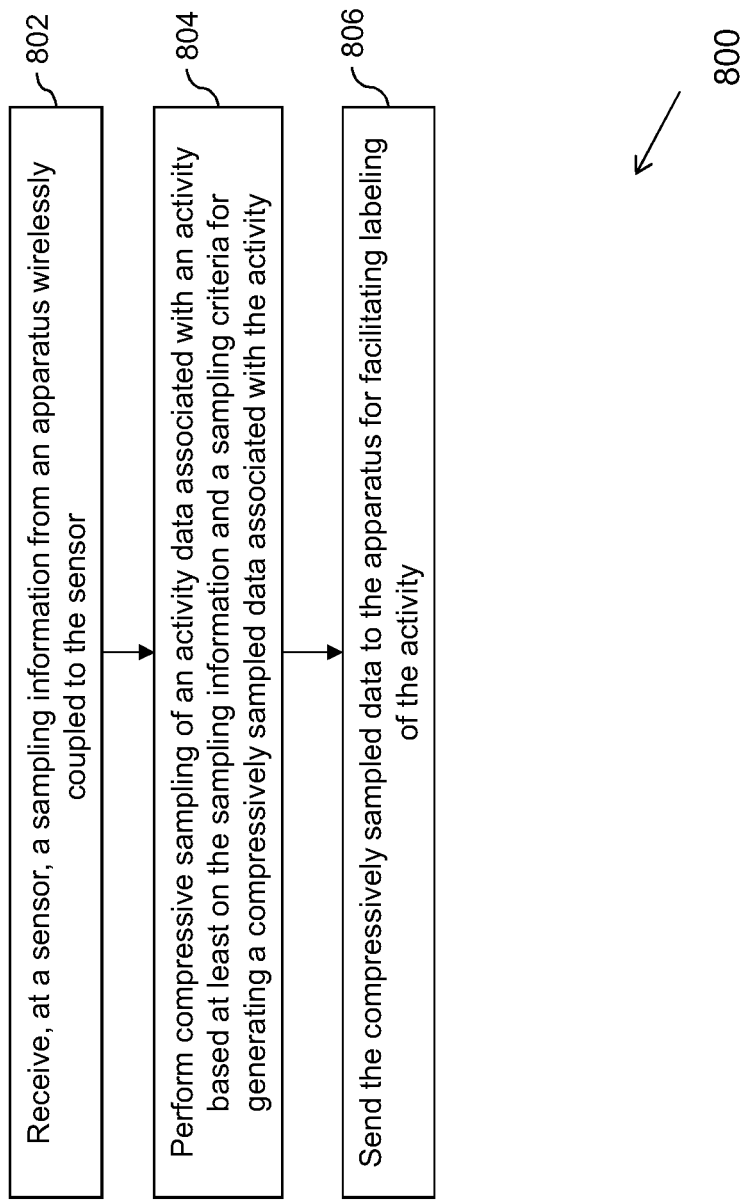
FIG. 8 is a flowchart depicting an example method for activity recognition, in accordance with another example embodiment.

FIG. 8 is a flowchart depicting an example method 800 for activity recognition, in accordance with an example embodiment. The method 800 depicted in the flow chart may be executed by, for example, the apparatus 400 of FIG. 4. For example, the method may executed by wearable sensors comprising the apparatus 400. The sensors may be attached to a user's body to measure an activity data associated with a user activity. In an embodiment, the activity data may include attributes such as motion, location, temperature, ECG, and the like. In an embodiment, examples of devices embodying the apparatus 400 may include sensors such as an accelerometer, a barometer, a compass, and the like.

At block 802, the method includes receiving a sampling information at an apparatus (for example, the apparatus 400, explained in FIG. 4) from another apparatus (for example, the apparatus 300, explained in FIG. 3) wirelessly coupled to the apparatus 400. Herein, apparatus 400 may be embodied in a sensor. Accordingly, the description of method 800 may be explained by referring apparatus 400 as sensor, and vice-versa. In an embodiment, the sampling information includes a basis matrix and a selection information for selecting at least a subset of the basis matrix. In an embodiment, the basis matrix may be a complete basis matrix wherein the basis vectors may span an entire predefined space as opposed to a subspace of the predefined subspace. In an embodiment, the complete basis matrix associated with the sampling information may be an N×N matrix.

At block 804, compressive sampling of the activity data may be performed based at least on the sampling information and a sampling criteria. In an embodiment, the compressive sensing may be performed to generate a sampled data associated with the activity. In an embodiment, the sampling criteria may include selection of an incoherent basis for performing compressive sampling. In an embodiment, the subset the complete basis matrix may be selected based on the selection information. For example, a set of M basis vectors may be selected from the complete basis matrix to form an M×N sampling matrix. The M×N sampling matrix may be denoted by 'A'. In an embodiment, the sampled data may be generated by performing compressive sampling of the activity data along with the set of basis vectors that may be randomly selected based on the sampling information. For example, a data vector (x) of length N (e.g. in time domain) may be projected along the set of basis vectors. The sampled data may be generated based on the expression:

$$y = A^T x,$$

where, A denotes the N×M sampling matrix whose columns are the (orthogonal) basis vectors, and x denotes the N dimensional uncompressed data vector At block 806, the sampled data may be sent to the apparatus (for example, the apparatus 300) for facilitating labeling of the activity. In an embodiment, the sampled data may be sent to the apparatus until a frame of the sampled data may be received at the apparatus. In an example embodiment, the frame size may be about 0.1 s-10 s. In an embodiment, the sampled data may be sent to the apparatus 300 over a wireless link.

Figure 9:
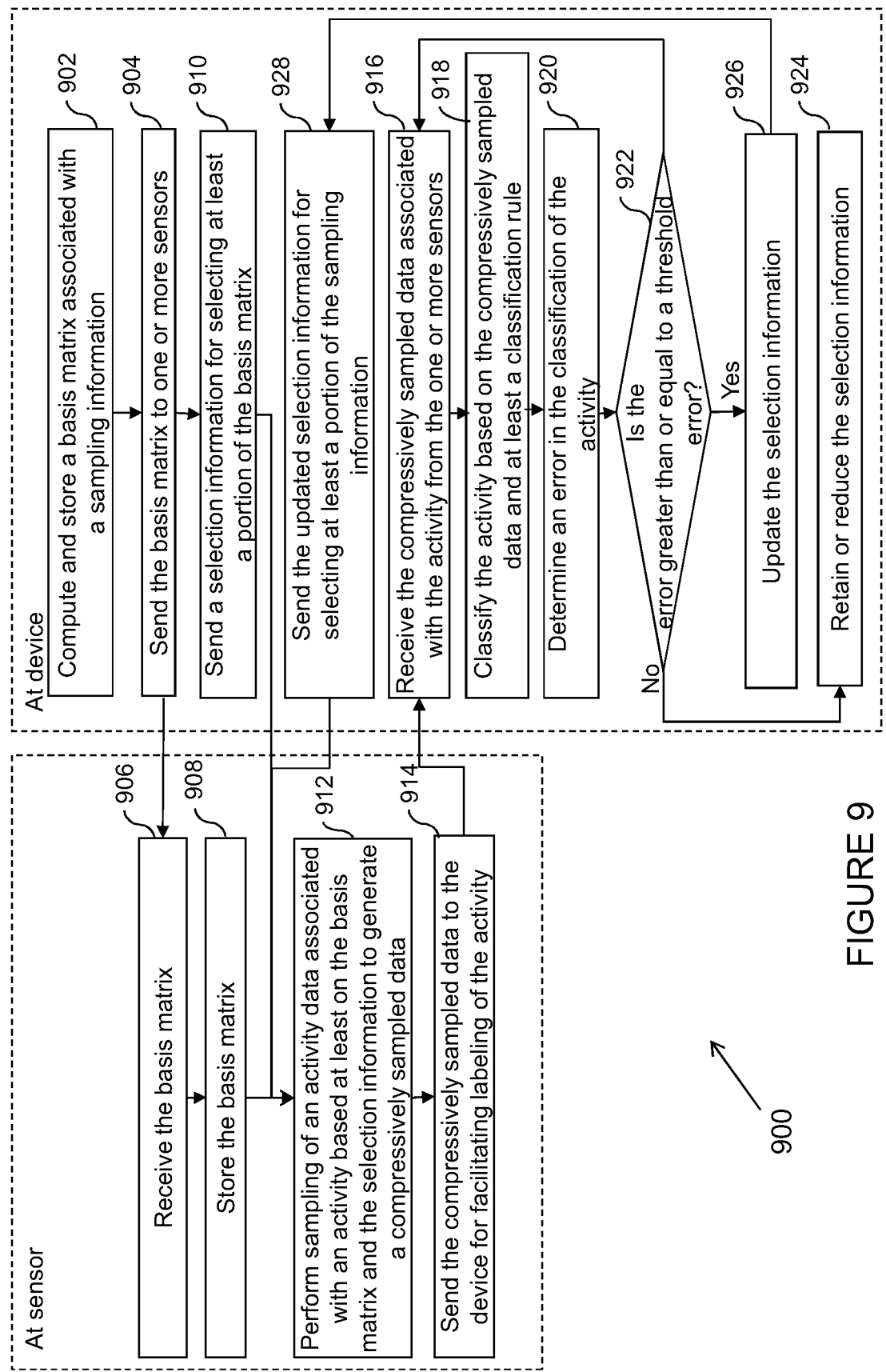
FIG. 9 is a flowchart depicting an example method for activity recognition, in accordance with yet another example embodiment.

FIG. 9 is a flowchart depicting an example method 900 for activity recognition, in accordance with an example embodiment. The method 900 depicted in the flow chart may be executed by, for example, the apparatuses 300 and 400 of FIGS. 3 and 4, respectively. Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of an apparatus and executed by at least one processor in the apparatus. Any such computer program instructions may be loaded onto a computer or other programmable apparatus (for example, hardware) to produce a machine, such that the resulting computer or other programmable apparatus embody means for implementing the operations specified in the flowchart. These computer program instructions may also be stored in a computer-readable storage memory (as opposed to a transmission medium such as a carrier wave or electromagnetic signal) that may direct a computer or other programmable apparatus to function in a particular manner, such that the instructions stored in the computer-readable memory produce an article of manufacture the execution of which implements the operations specified in the flowchart. The computer program instructions may also be loaded onto a computer or other programmable apparatus to cause a series of operations to be performed on the computer or other programmable apparatus to produce a computer-implemented process such that the instructions, which execute on the computer or other programmable apparatus provide operations for implementing the operations in the flowchart. The operations of the method 900 are described with help of apparatus 300 and 400 of FIGS. 3 and 4, respectively. However, the operations of the method can be described and/or practiced by using any other apparatus.

The method 900 provides steps for activity recognition in context-awareness based applications. Examples of activities that may be utilized for activity recognition may include walking, jogging, running, and the like. In an embodiment, one or more sensors may acquire and process data associated with user activities. In an embodiment, one or more sensors may be embodied in one or more wearable devices that may be attached to a user's body so as to acquire activity data by measuring various attributes associated with activity recognition. For example, the one or more sensors may be configured to measure motion, location, temperature, humidity, audio level and other such attributes required for activity recognition. In an embodiment, the one or more sensors may process the acquired data and send the processed activity data to the apparatus 300. In an embodiment, the apparatus 300 may be embodied in a device, for example the device 200 (explained with reference to FIG. 2). The device 200 may utilize the processed activity data to classify the "activity" of the user. An information regarding the user's activity may be utilized to provide activity-dependent user experiences.

At block 902 of method 900, a basis matrix associated with a sampling information may be computed at the device, for example the device 200. In an embodiment, the sampling information may include the basis matrix and a selection information for selecting at least a subset of the basis matrix. In an embodiment, the sampling information may be stored, for example in a memory of the apparatus 300. At block 904, the sampling information may be sent to the one or more apparatus, for example the apparatus 400 (explained with reference to FIG. 3). In an embodiment, the one or more apparatus 300 may include one or more sensors. In an embodiment, the one or more apparatus 300 may be communicatively coupled with the device 200. In an embodiment, the one or more sensors may be coupled with the apparatus 300 through a wireless link.

At block 906, the one or more sensors may receive the basis matrix. At block 908, the one or more sensors may store the basis matrix. In an embodiment, the one or more sensors may store the basis matrix in a memory, for example the memory 406 (refer to FIG. 4).

At block 910, the device 200 may send a selection information to the one or more sensors for selecting a subset of the basis matrix. In an embodiment, the selection information includes instructions for selecting the subset of the complete basis matrix. In an embodiment, the instructions may include one or more basis vectors and a basis size that may be selected from the complete basis matrix.

At block 912, a sampling of an activity data associated with a user activity is performed. In an embodiment, the sampling of the activity data is performed at the one or more sensors. In an embodiment, the sampling of the activity data is performed based at least on the complete basis matrix and the selection information received from the device 200. In an embodiment, sampling may be performed based on compressive sampling by utilizing an incoherent basis.

In an embodiment, the activity data may be sampled along with the set of basis vectors that may be randomly selected based on the sampling information. A data vector (denoted by x) of length N (e.g. in time domain) may be projected along the set of basis vectors. The projection of the data vector along the set of randomly selected basis vectors is explained with reference to FIG. 5. Based on sampling, the sampled data may be generated as per the following expression:

$$y = A^T x,$$

where, A denotes an N×M sampling matrix whose columns are the (orthogonal) basis vectors, and x denote the N dimensional uncompressed data vector associated with the activity data.

At block 914, the sampled data may be sent by the one or more sensors to the device. In an embodiment, the sampled data may facilitate in labeling of the activity at the device. At block 916, the sampled data sent by the one or more sensors may be received at the device. At block 918, the activity may be classified based at least on the sampled data and a classification rule. In an embodiment, the classification of the activity may include assigning a label to the activity. In an embodiment, the classification rule may include a model comprising a training set of labeled samples. In an example embodiment, the training set with labels may be represented in the basis that is utilized for sampling of the activity data at the one or more sensors. In another example embodiment, the labels in the training set may be provided initially (e.g. as in "factory settings") in a complete basis from which it is easy to calculate the set in any undercomplete basis such as the one used for compressive sampling of the activity data. In another embodiment, the labels associated with the training set may be deduced from other sensory data. In yet another example embodiment, the labels may be obtained based on an unsupervised learning. For example, various identify clusters (e.g. k-means algorithm) may be generated and labels may be obtained by "asking" information from the user.

In an embodiment, the sampled data output from the one or more sensors may include error due to noise or minute perturbations in the activity data observed by the one or more sensors. Since the activities performed by the users do not undergo substantial fluctuation over a very short time scale (for example, seconds), a variance in the output of the classification output may be utilized for detection of any errors in the classification. At block 920, an error in the sampled data may be determined. In an example embodiment, an error correction may be applied to the output of the classification. In an example embodiment, an error correction mechanism may include majority voting. It will be understood that certain other complex correlations may also be utilized for applying error correction to the classification output.

At block 922, it may be determined whether is error in the classification of the activity is greater than a threshold error. In an embodiment, the threshold error may be fixed prior to performing sampling of the activity data. In an embodiment, on detection of absence of any errors in classification, the number of vectors associated with the sampling information may be retained or reduced. In an embodiment, the size of the sampling matrix may be reduced by reducing the number of vectors therein. In an alternate embodiment, the size of the sampling matrix may be retained as such as block 924, if the size of the sampling matrix is determined to be already at a minimum allowable size. In an embodiment, the minimum allowable size of the matrix may be preset in the device.

In an embodiment, on determination of error being greater than or equal to the threshold error, the compressive sampling metrics may be updated at block 926. For example, based on the determined number of error to be greater than the threshold error, the number of vectors may be increased. Additionally or optionally, if the error associated with previous predetermined number of times is determined to be greater than the threshold error, then the size of the basis matrix associated with the sampling information may be increased.

At block 928, the updated selection information may be sent to the one or more sensors for selecting at least a portion of the sampling information. In an embodiment, the at least the portion of the sampling information selected based on the updated selection information is different from the subset of sampling information that was previously utilized for generating the sampled data. In an embodiment, the at least a portion of the sampling information selected based on the updated selection may be utilized for reclassifying the activity.

To facilitate discussion of the methods 700, 800 and/or 900 of FIGS. 7, 8 and 9, certain operations are described herein as constituting distinct steps performed in a certain order. Such implementations are exemplary and non-limiting. Certain operation may be grouped together and performed in a single operation, and certain operations can be performed in an order that differs from the order employed in the examples set forth herein. Moreover, certain operations of the methods 700, 800 and/or 900 are performed in an automated fashion. These operations involve substantially no interaction with the user. Other operations of the methods 700, 800 and/or 900 may be performed by in a manual fashion or semi-automatic fashion. These operations involve interaction with the user via one or more user interface presentations.

Without in any way limiting the scope, interpretation, or application of the claims appearing below, a technical effect of one or more of the example embodiments disclosed herein is to perform activity recognition. As explained in FIGS. 1-9, The embodiments disclosed herein provide methods and devices for performing activity recognition. In various embodiments, the devices such as distributed sensors may be configured to acquire data and process the acquired data. The acquired data may be processed based on compressive sampling. The processed data (or the sampled data) may be sent wirelessly to a device (for example a smartphone). The device utilizes the sampled data directly for classifying the "activity" of the user. In an embodiment, the information about the activity can then be used to provide activity-dependent user experiences. The disclosed method and devices are advantageous since the sampled data may be utilized directly for performing activity recognition, thereby precluding a need for decompression. Additionally, since the sampled data may be directly utilized for activity recognition, the disclosed methods and devices facilitates low bandwidth requirement and a lower power consumption. Also, since the data is compressively sampled at the wireless devices, it can be economically transmitted and stored on the central device. Further, using "random" sampling provides a degree of privacy as it may not be easy to deduce everything from the data without knowing the sampling basis. The information about the basis to be used may only be stored on the user's device or other secure storage. In an embodiment, the classification may be performed even below the decompression threshold. Moreover, the activity data automatically undergoes a dimensionality reduction step which is beneficial for classification/machine learning.

Various embodiments described above may be implemented in software, hardware, application logic or a combination of software, hardware and application logic. The software, application logic and/or hardware may reside on at least one memory, at least one processor, an apparatus or, a computer program product. In an example embodiment, the application logic, software or an instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer, with one example of an apparatus described and depicted in FIGS. 3 and/or 4. A computer-readable medium may comprise a computer-readable storage medium that may be any media or means that can contain or store the instructions for use by or in connection with an instruction execution system, apparatus, or device, such as a computer. In one example embodiment, the computer readable medium may be non-transitory.

If desired, the different functions discussed herein may be performed in a different order and/or concurrently with each other. Furthermore, if desired, one or more of the above-described functions may be optional or may be combined.

Although various aspects of the embodiments are set out in the independent claims, other aspects comprise other combinations of features from the described embodiments and/or the dependent claims with the features of the independent claims, and not solely the combinations explicitly set out in the claims.

It is also noted herein that while the above describes example embodiments of the invention, these descriptions should not be viewed in a limiting sense. Rather, there are several variations and modifications, which may be made without departing from the scope of the present disclosure as defined in the appended claims.

We claim:

1. A wearable apparatus comprising:
   at least one processor; and
   at least one memory comprising computer program code, the at least one memory and the computer program code configured to, with the at least one processor, cause the wearable apparatus to at least:
   receive, at the wearable apparatus, sampling information comprising a basis matrix and selection information from a second apparatus wirelessly coupled to the wearable apparatus, wherein the wearable apparatus is embodied by a wearable device configured to be attached to a user;
   perform an initial compressive sampling of an activity data associated with an activity that comprises a human behavior in the form of an action or a movement by the user, wherein the compressive sampling is performed based at least on the sampling information and a sampling criteria for generating a sampled data associated with the activity, wherein the activity data is measured by one or more sensors of the wearable device, wherein the initial compressive sampling is carried out such that a basis size of the sampled data is within a predetermined range, said basis size being previously known by the wearable apparatus and shared with the second apparatus;
   send the sampled data to the second apparatus for facilitating classification of the activity;
   receive, in an instance in which an error satisfying a threshold error in the classification of the activity, updated selection information from the second apparatus;
   perform, in response to receiving the updated selection information, a subsequent compressive sampling of the activity data based at least on the updated selection information and the sampling criteria to generate updated sampled data having an updated basis size greater than the basis size, wherein the updated basis size is determined dynamically based on said error in the classification of the activity; and
   send the updated sampled data to the second apparatus for facilitating reclassification of the activity.

2. The wearable apparatus according to claim 1, wherein the wearable apparatus is further caused, at least in part, to store the sampling information.

3. The wearable apparatus according to claim 1, wherein the sampling information comprises a basis matrix comprising basis vectors and the selection information for selecting a basis size and a subset of basis vectors from the basis matrix.

4. The wearable apparatus according to claim 3, wherein the updated selection information has an increased basis size associated with the subset of the basis matrix.

5. The wearable apparatus according to claim 3, wherein the updated selection information has an increased number of basis vectors.

6. The wearable apparatus according to claim 1, wherein the wearable apparatus is further caused, at least in part, to:
   select the subset of the basis matrix based at least on the selection information.

7. The wearable apparatus according to claim 1, wherein the wearable apparatus is further caused, at least in part, to:
   send the sampled data to the second apparatus for facilitating classification of the activity until a frame of the sampled data is sent to the second apparatus.

8. The wearable apparatus according to claim 1, wherein the wearable apparatus is further caused, at least in part, to:
   generate, at the wearable apparatus, the basis matrix associated with a space; and
   store the basis matrix in the at least one memory of the wearable apparatus.

9. The wearable apparatus according to claim 8, wherein the selection information comprises instructions for selecting a subset of the basis matrix, and wherein the wearable apparatus is further caused, at least in part, to either:
   select the subset of the basis matrix; or
   cause the second apparatus to select the subset of the basis matrix.

10. The wearable apparatus according to claim 9, wherein the instructions comprise one or more basis vectors and the basis size, the one or more basis vectors and the basis size operable to be selected from the basis matrix.

11. The wearable apparatus according to claim 10, wherein one or more of the initial compressive sampling and the subsequent compressive sampling is performed utilizing an incoherent basis.

12. The wearable apparatus according to claim 1, wherein the wearable apparatus is further caused, at least in part, to:
provide, based at least upon the reclassification of the activity by the user, activity-dependent user experiences.

13. The wearable apparatus according to claim 1, wherein the activity is classified based at least on the sampled data and a classification rule.

14. The wearable apparatus according to claim 13, wherein the classification rule comprises a model comprising a training set of labeled samples.

15. The wearable apparatus according to claim 14, wherein the training set is represented in the basis matrix that is utilized for said sampling of the activity data or the training set is provided initially in a complete basis, said complete basis operable for calculating a set in any undercomplete basis used for compressive sampling of the activity data.

16. The wearable apparatus according to claim 13, wherein labels associated with the training set are obtained using an unsupervised learning algorithm.

17. The wearable apparatus according to claim 13, wherein labels associated with the training set are deduced from other sensory data received at or measured by the wearable apparatus or the second apparatus.

18. The wearable apparatus according to claim 1, wherein the error is determined based upon one or more variances in an output of the classification of the activity.

19. The wearable apparatus according to claim 1, wherein the wearable apparatus is further caused, at least in part, to:
cause the second apparatus to apply an error correction to the output of the classification.

20. The wearable apparatus according to claim 19, wherein the error correction comprises a majority voting complex correlation approach.

21. The wearable apparatus according to claim 1, wherein the updated selection information received from the second apparatus is operable for selecting at least a portion of the sampling information, wherein the at least the portion of the sampling information selected based on the updated selection information is different from the subset of sampling information utilized for generating the sampled data.

22. The wearable apparatus according to claim 21, wherein the at least a portion of the sampling information selected based on the updated selection information is operable to be utilized for reclassifying the activity.

* * * * *